United States Patent [19]
Noboru

[11] 4,093,385
[45] June 6, 1978

[54] COLOR GRADIENT ANALYZER

[75] Inventor: Murata Noboru, Tokyo, Japan

[73] Assignee: Oki Electric Industry Co., Ltd., Tokyo, Japan

[21] Appl. No.: 730,472

[22] Filed: Oct. 7, 1976

[30] Foreign Application Priority Data

Oct. 17, 1975  Japan ............................. 50-124407

[51] Int. Cl.² ........................... G01J 3/48; G01J 1/02
[52] U.S. Cl. ..................... 356/188; 250/226; 356/243
[58] Field of Search .............. 356/188, 189, 243; 250/226

[56] References Cited

U.S. PATENT DOCUMENTS

| | | | |
|---|---|---|---|
| 3,776,642 | 12/1973 | Anson et al. | 356/188 |
| 3,811,781 | 5/1974 | Lowy | 356/188 |
| 3,828,173 | 8/1974 | Knepler | 356/188 |
| 3,861,788 | 1/1975 | Webster | 356/188 |
| 4,029,419 | 6/1977 | Schumann, Jr. et al. | 356/189 |

Primary Examiner—Vincent P. McGraw
Attorney, Agent, or Firm—Kenyon & Kenyon

[57] ABSTRACT

A color gradient analyzer having a photo-electric convertor and a rotational filter having a plurality of optical color filters provides the information of an object. The output of said photo-electric convertor is switched according to the color of the color filter of said rotational filter in front of the photo-electric convertor, and is recorded on a recorder. A white ball is also provided for the calibration of the apparatus. Thus the apparatus can operate and provide a color information on a real-time basis.

6 Claims, 3 Drawing Figures

COLOR GRADIENT ANALYZER

BACKGROUND OF THE INVENTION

The present invention relates, in general, to a color gradient analyzer or a spectrum analyzer, and in particular, relates to a device for recognizing the contamination or the dirt content of an ocean or a river by analyzing the color spectrum of the water surface of an ocean or a river.

A prior spectrum analyzers operate on the principle of physical optics. However, prior spectrum analyzers have the disadvantage that it is difficult to measure, on a real-time basis, the surface color of an ocean or a river which changes from one minute to the next. Because of the severe nature of ocean and river pollution in recent times, a real-time measurement of the color of the water surface is desired for keeping clean an ocean or a river, recognizing the change of an ocean current, and for recognizing the presence of red water.

SUMMARY OF THE INVENTION

It is an object, therefore, of the present invention to overcome the disadvantage of prior spectrum analyzers by providing a new and improved color gradient analyzer.

It is also an object of the present invention to provide a new and improved color gradient analyzer which operates on a real-time basis.

The above and other objects are attained by a color gradient analyzer comprising a rotational filter having a plurality of color filters, a photo-electric convertor positioned observable an object to be analyzed through one of said filters, a white ball for calibrating the apparatus, means for recording the output of the photo-electric convertor, and means for switching the output of the photo-electric convertor according to the color of a color filter in front of the photo-electric convertor.

BRIEF DESCRIPTION OF THE DRAWINGS

The foregoing and other objects, features, and attendant advantages of the present invention will be appreciated as the same become better understood by means of the following description and the accompanying drawings wherein.

DESCRIPTION OF THE PREFERRED EMBODIMENT

Figure 1:
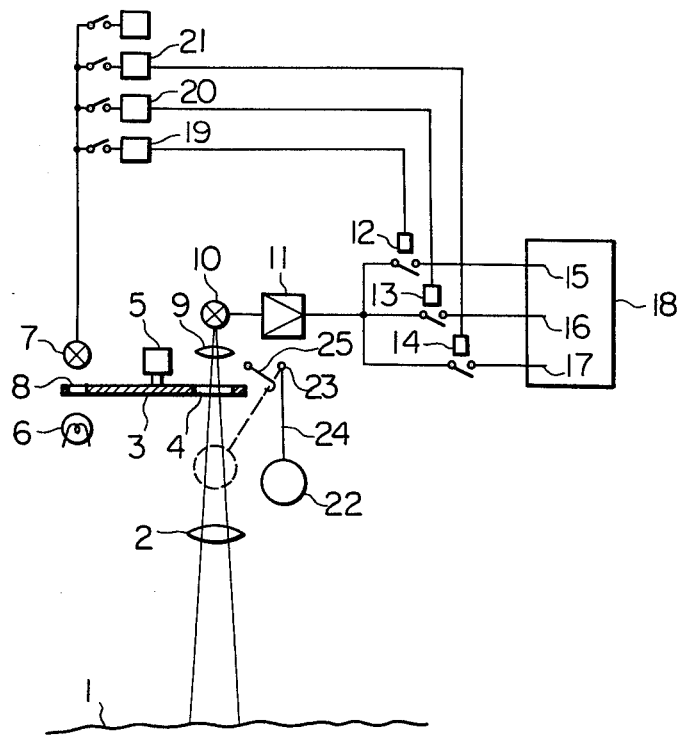
FIG. 1 shows the block-diagram of the color gradient analyzer according to the present invention.

FIG. 1 shows the block-diagram of the present color gradient analyzer. In FIG. 1, the reference numeral 1 shows a sea surface, 2 is an object glass, 3 is a rotational filter, which is shown in detail in FIG. 2. The rotational filter 3 has on the periphery of the same a plurality of optical filters 4, 4a, 4b and 4c, which are red, yellow, blue and purple, respectively. The rotational filter 3 also has a small hole 8. Said rotational filter is coupled to the motor 5, which rotates at a constant speed. A light 6 throws a light beam through the hole 8 to the photo-electric convertor 7. The reference numeral 9 is a condenser lens, 10 is a photo-electric convertor, 11 is an amplifier, 12, 13, and 14 are relays, and, 15, 16 and 17 are recording pens for converting an electrical signal into graph form on a recorder 18. The pens 15, 16 and 17 operate when the relays 12, 13 and 14 close, respectively. The reference numerals 19, 20 and 21 are delay circuits which delay a signal from the photo-electric convertor 7, and supply the delayed signals to the relays 12, 13 and 14. 22 is a white ball provided between the lens 2 and the filter 4, and said white ball 22 is fixed at the end of the arm 24, the other end of which may be pivoted around the supporting point 23 near the lens 2. When the white ball 22 interrupts the light beam between the lens 2 and the filter 4, the ball is fixed in position by the hook 25.

The apparatus of FIG. 1 operates in two modes.

In mode 1, the apparatus is calibrated, and in mode 2 measurement of the spectrum is performed.

Figure 2:
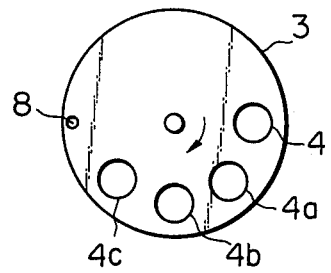
FIG. 2 shows a plane view of a rotational filter and FIG. 3 is an embodiment of the written chart by the present apparatus.
Figure 3:
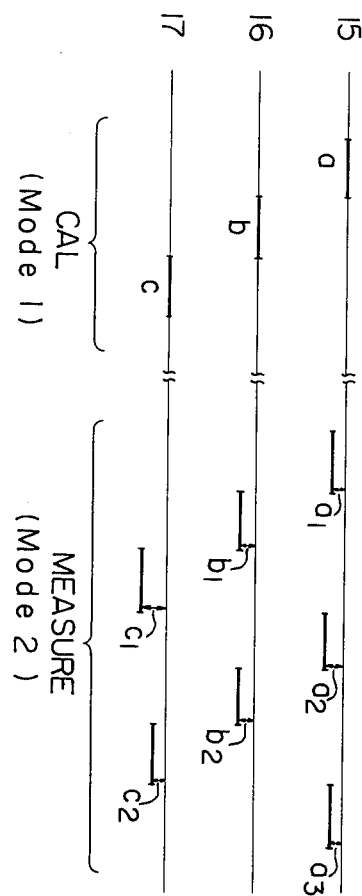

In mode 1, the white ball 22 is positioned as indicated by the dotted line in FIG. 1 and interrupts the light from the sea surface 1 to the rotational filter 3. The arm 24 is fixed by the hook 25 so that the white ball 22 is positioned to the above position. In this case, the sun light reflected by the white ball 23 goes through the filters 4, 4a, 4b or 4c and the condenser lens 9 to the photo-electric convertor 10, which provides the electric signal related to the strength of the light to the convertor 10. The convertor 10 is embodied by a photo-diode or a photo-multiplier. Said electric signal is applied to the contacts of the relays 12, 13 and 14 through the amplifier 11, which amplifies the input electric signal and shapes the waveform of the same to a rectangular form. The relays 12, 13 and 14 are closed by the control of the delay circuits 19, 20 and 21, which receive the electric signal from the photo-electric convertor 7. The photo-electric convertor 7 provides the electric signal according to the passage of the hole 8 under the convertor 7, and said electric signal from the convertor 7 functions as the synchronizing signal of the apparatus. The delay circuit 19 delays the electric signal from the convertor 7 and provides the output signal to the winding of the relay 12 just when the related filter 4a is passing under the condenser lens 9. Similarly, the delay circuits 20 and 21 delay the electric signal so as to provide the output signal to the relays 13 and 14 just when the filters 4b and 4c are passing under the c condenser lens 9, respectively. Accordingly, the contact of the relays 12, 13 and 14 is closed just when the filters 4a, 4b and 4c are passing under the lens 9, respectively, and thus, the recording pens 15, 16 and 17 of the recorder 18 record the amplitude relating to the strength of the light passed through the filters 4a, 4b and 4c, respectively. From the above explanation, it is clear that the delay circuits 19, 20 and 21 function as a gate circuit to open and/or close the contact of the relays 12, 13 and 14. A delay circuit can be embodied by a digital counter using an I. C. (Integrated Circuit). When the apparatus is calibrated, the recording pens 15, 16 and 17 record the lines a, b and c, respectively, as shown in FIG. 3. The amplitude or the position of the lines a, b and c relate, of course, to the strength of the light received by the convertor 10 through the filters 4a, 4b and 4c. In FIGS. 1, 2 and 3, only three or four sets of filters (4, 4a, 4b, 4c), delay circuits (19, 20, 21), relays (12, 13, 14), and recording pens (15, 16, 17), are shown for the simplicity of the explanation. It should be understood of course that the number of filters, delay circuits, relays and recording pens can be designed arbitrary.

Next, the measurement of the color gradient on a water surface is performed in mode 2, in which the hook 25 is released and the white ball 22 is removed to the position indicated by the solid line in FIG. 1. Accordingly, the light reflected by the sea surface 1 is received by photo-electric convertor 10 through the object glass 2, the rotational filter 3 and the condenser lens 9. Thus the information concerning the color of the sea surface is recorded on the recorder 18 by the recording pens 15, 16 and 17. It should be understood of course that the information recorded by the pens 15, 16 and 17 relates to the filters 4a, 4b and 4c, respectively. The example of the written record is shown in FIG. 3. The color information thus measured, is compared with the calibrated value in mode 1, and the difference between the calibrated value and the measured value, $a_1, a_2, a_3, \ldots, b_1, b_2, b_3, \ldots, c_1, c_2, c_3, \ldots$, is obtained. Those differences show the color information of the sea surface. If the rotational filter 3 rotates at a speed of 360°/sec, the color information is obtained every second. From the color information thus obtained, the condition of the sea surface, like the presence of the red water or the water pollution can be analyzed.

Some modifications of the present invention are of course possible. For instance, the recorder 18 can be replaced by an electronic memory, in which the calibrated value is stored in the memory and the output concerning the color information is obtained in the form of a frequency modulated signal, a phase modulated signal or an amplitude modulated signal.

When only one or two color informations are requested, a switch between the photo-electric convertor 7 and the delay circuits will remove the unnecessary curves in FIG. 3, and only one or two of the pens 15, 16 and 17 will operate.

Further, an air-plane having the present apparatus can measure the color of surface of a sea, a river or a lake on a real-time basis, and transmit the measured result to a central processor, and the measured result can be utilized in meterological observations, fishing industry and the prevention of the pollution.

In order to avoid the influence of the brightness of the image of the sun, it is preferable to design movable the optical means including the objective glass 2, the condenser lens 9, the rotational filter 3, the photo-electric convertors 7 and 10, and the lamp 6.

As apparent from the above explanation, the real-time observation of a water surface has become possible. It should be understood of course that the embodiment disclosed is merely illustrative and is not intended to limit the scope of the invention. Reference should be made to the appended claims, therefore, rather than the specification as indicating the scope of the invention.

What is claimed is:

1. A color gradient analyzer comprising a rotational filter having a plurality of optical color filters, a motor for rotating the rotational filter, a photo-electric converter positioned observable an object illuminated by the natural sun to be analyzed through one of said color filters, a white ball positionable between the photo-electric converter and an object to be analyzed, said white ball being able to be illuminated by the sunlight, a plurality of relays connected to the output of the photo-electric converter, a recorder connected to the outputs of said relays, means for providing the signal concerning the rotational angle of the rotational filter, and a plurality of delay circuits connected between said means and said relays.

2. A color gradient analyzer according to claim 1, further comprising a switch connected between the output of said means for providing rotational angle of the rotational filter and the input of one of the delay circuits.

3. A color gradient analyzer according to claim 1, further comprising an amplifier for amplifying the output of the photo-electric convertor and shaping the waveform of the same to a square wave, connected between the photo-electric convertor and the relays.

4. A color gradient analyzer according to claim 1, wherein the rotational speed of the rotational filter is about 360°/second.

5. A color gradient analyzer according to claim 1, further comprising an object glass and a condenser lens provided between the photo-electric converter and an object to be analyzed.

6. A color gradient analyzer according to claim 1, wherein said means for providing the signal concerning the rotational angle of the rotational filter, comprises a fixed photo-electric convertor, a small hole on said rotational filter, and a fixed lamp positioned so as to throw a light beam to said photo-electric convertor through said hole.

* * * * *